United States Patent [19]

Koltisko

[11] Patent Number: 5,256,417
[45] Date of Patent: Oct. 26, 1993

[54] WATER DISPERSIBLE TOWELETTE IMPREGNATED WITH NON-AQUEOUS LOTION FORMULATIONS

[75] Inventor: Bernard M. Koltisko, Emmanus, Pa.

[73] Assignee: Air Products and Chemicals, Inc., Allentown, Pa.

[21] Appl. No.: 830,045

[22] Filed: Jan. 31, 1992

[51] Int. Cl.$^5$ .............................. A01N 25/34
[52] U.S. Cl. ...................... 424/402; 428/74; 428/249; 428/490
[58] Field of Search .............. 424/402; 428/490, 249, 428/74

[56] References Cited

U.S. PATENT DOCUMENTS

| | | | |
|---|---|---|---|
| 3,645,836 | 2/1972 | Torr | 428/284 |
| 3,922,434 | 11/1975 | Lindgren | 428/342 |
| 4,258,849 | 3/1981 | Miller | 206/812 |
| 4,309,469 | 1/1982 | Varona | 428/74 |
| 4,343,403 | 8/1982 | Daniels et al. | 206/812 |
| 4,624,890 | 11/1986 | Lloyd | 428/249 |
| 4,725,489 | 2/1988 | Jones | 428/290 |
| 4,904,524 | 2/1990 | Yoh | 424/402 |

*Primary Examiner*—Thurman K. Page
*Assistant Examiner*—D. Gabrielle Phelan
*Attorney, Agent, or Firm*—Michael Leach; James C. Simmons; William F. Marsh

[57] ABSTRACT

A packaged towelette composed of a sheet of nonwoven fibers impregnated with a binder which is a polyvinyl alcohol or an aqueous polymer emulsion containing polyvinyl alcohol as the protective colloid, the sheet being maintained in a wet condition within the package by contact with a nonaqueous lotion composition which is a liquid organic compound that is a nonsolvent for polyvinyl alcohol.

10 Claims, No Drawings

WATER DISPERSIBLE TOWELETTE IMPREGNATED WITH NON-AQUEOUS LOTION FORMULATIONS

FIELD OF THE INVENTION

This invention relates to a pre-moistened nonwoven towelette that is readily disposable.

BACKGROUND OF THE INVENTION

The issue of disposability of products is a great concern to the nonwovens industry. Landfills, incineration, multiple sewage treatment and residential septic systems are among the common choices for nonwoven product disposal today. Products targeted for the latter disposal routes via residential and commercial toilets are termed flushable. Current flushable products have limitations. Dry products, such as bathroom tissue, have been designed with minimal wet strength so that the tissue can disintegrate under the agitation in the plumbing systems. They are not designed for applications where water will be encountered in use. Flushable wet wipes have high wet strengths and do not lose their strength upon disposal. These products remain intact and identifiable in the disposal system.

Wet-packaged skin cleansing and refreshing tissues are well known commercially, generally referred to as towelettes, wet wipes, fem wipes and the like. These may comprise an absorbent sheet made of paper, prepared or treated to impart wet strength thereto, having the dimensions of the usual washcloth and packaged wet in folded condition individually in impervious envelopes or in multiples in closed containers. The liquid employed in premoistening the sheet is generally an aqueous alcoholic solution which may further contain a surface active detergent and a humectant and, in some instances, also a scenting agent. Instead of individual packaging of such moist sheets, they are often marketed in reclosable containers having any desired convenient number of such folded sheets.

U.S. Pat. Nos. 4,258,849 and 4,343,403 disclose pre-moistened towelettes which are flushable. These towelettes incorporate a polyvinyl alcohol (PVOH) or PVOH stabilized emulsion as a binder, respectively, and an aqueous pre-moistening lotion which contains salts (especially boric acid) that insolubilize the PVOH to impart good strength and integrity. Relatively high salt concentrations are required to impart good strength. For example, useful performance is not achieved until at least 3% boric acid is used. All other useful insolubilizing salts for PVOH need to be used at much higher concentrations to achieve the same effect. Wipes prepared with these types of binders rapidly disintegrate by reduction in salt concentration and solubilization of the PVOH based binder.

However, the salt containing formulations cannot be used in some applications such as cleaning wipes or some personal care wipes where lotion residues due to the salts are not acceptable. These salts are not volatile and will deposit as streaks or white powdery residue on the surface as the lotion evaporates.

There is a desire in the nonwovens industry to make cleaning wipe products which do not leave residues such as bathroom or hospital disinfecting wipes which can also be disposed of in the toilet after use.

There is a general need to supply non-water based medical, cosmetic or personal care formulations by means of a pre-moistened towelette. These formulations may come in contact with body fluids, which for sanitary reasons, may then be disposed of in the toilet. These products to date have been applied to small towelettes since they are incapable of disintegration upon disposal in water. Large size or high number of these products would result in clogging of the plumbing systems. Also, pre-moistened towelettes manufactured today are not generally recyclable or easily degraded in the environment due to their use of non-water redispersible binders such as vinyl acetate/ethylene/N-methyolacrylamide (VAE/NMA) copolymers.

This problem of salt residue has been partially addressed in U.S. Pat. No. 4,309,469. The use of multi-component binder formulations and multi-component lotion salt compositions are described in which total salt concentration is reduced to 1%. This level is still too high to solve the problem. In general, this issue has not been addressed since the PVOH/salt technology has not been targeted for surface cleaning applications. The market for pre-moistened wipes is rapidly growing and new products containing specific lotion cleaning fluids have just entered the market. These current products do not disintegrate in water and are not designed to be disposed in the toilet.

SUMMARY OF THE INVENTION

The present invention provides wet-packaged cloths made of nonwoven fibers coated or impregnated with a binder to impart wet strength. The binder may be a PVOH or an aqueous polymer emulsion containing PVOH as the protective colloid. The cloths are packaged in contact with a non-aqueous lotion comprising a liquid organic compound that is a nonsolvent for PVOH.

The pre-moistened towelette of useful dimensions comprising nonwoven fibers, binder and impregnating lotion exhibits good strength while stored in a sealed package and during use, and yet the towelette rapidly disintegrates in plain tapwater.

DETAILED DESCRIPTION OF THE INVENTION

The initial treatment to coat or impregnate the nonwoven fabric, such as absorbent paper, with the PVOH or PVOH stabilized polymer emulsion may be carried out by immersing the webs or running lengths of the fabric in an aqueous solution of the PVOH or in the aqueous polymer emulsion or by applying such solution or emulsion to the surfaces of the nonwoven web of fibers by spraying, by patting, by roller or other types of applicator. Following drying, the treated nonwoven web may then be cut to desired size sheets for the intended use. If desired, of course, individual sheets pre-cut to desired size may be treated with the aqueous PVOH solution or polymer emulsion.

The fibers may be any of the natural and synthetic fibers. Wood pulp (alone or blended with natural or synthetic fibers) processed by dry (airlaid, carded, rando) or wetlaid processes can be used. Nonwoven webs produced by airlaid processes are preferred due to minimal hydrogen bonding of fibers in the finished product compared to wetlaid nonwovens. Airlaid processes impart little or no inherent integrity to the web which must be overcome with agitation to achieve complete disintegration of the web.

The nonwoven binders suitable for use in the invention include 75 to 90 mole % hydrolyzed, preferably 86-89 mole % hydrolyzed, PVOH's alone or blended with polymer emulsions. It is preferred to use a PVOH having a high molecular weight (DPn greater than 600 and ranging up to 2500 and more) due to its lower solubility in organic solvents and its high film strength. It is also preferred that the emulsion polymer be non-crosslinking, e.g., does not contain polymerized N-methylolacrylamide, and most desirably contain PVOH as the protective colloid, or stabilizing system, in its preparation by aqueous emulsion polymerization. PVOH stabilized vinyl acetate (VAc) or vinyl acetate/ethylene (VAE) polymer emulsions are preferred due to their ease of water dispersibility. The ratio of PVOH to emulsion solids will depend upon the type of product being made and the choice of the emulsion. The preferred range is a minimum 20 parts PVOH (dry) to 100 parts emulsion (dry) up to and including 100% PVOH, i.e., no emulsion polymer binder. The VAE's tend to be more hydrophobic and better film formers than the VAc homopolymers and require, accordingly, higher amounts of PVOH, i.e., up to 200 parts PVOH per 100 parts emulsion (dry) compared to VAc homopolymers which may require up to 100 parts PVOH per 100 parts emulsion (dry).

The amount of polymer binder, calculated on a dry basis, applied to the fibrous starting web, is that amount which is at least sufficient to bind the fibers together to form a self-sustaining web and suitably ranges from about 3 to about 100% or more by weight of the starting web. Where PVOH is the polymer binder, about 3 to 20 wt % preferably is applied to the web. Where an aqueous polymer emulsion containing PVOH is the binder, about 5 to 50 wt % preferably is applied, the emulsion containing 20 to 200 parts PVOH per 100 parts emulsion on a dry basis.

The impregnated web is then dried by passing it through an air oven or the like for sufficient times and temperatures, such as drying at 150°–200° F. (66°–93° C.) for four to six minutes (in lab tests designed to simulate production conditions).

Lotion compositions comprising liquid organic compounds that are nonsolvents for PVOH are critical to the invention. Essentially all nonsolvents (including both volatile and non-volatile compounds) for PVOH as defined in the Polymer Handbook (second edition) page IV-246 would be appropriate. Such nonsolvent liquids would include hydrocarbons, halogenated hydrocarbons, lower alcohols, tetrahydrofuran, dioxane, ethylene glycol formal, ketones, carboxylic acids, esters, and ethyl lactate. The preferred lotion compositions comprise lower alcohols such as methanol, ethanol and iso- and n-propanols. These alcohols are selected for their volatility and would be highly appropriate for bathroom cleaning applications when a lotion must volatilize leaving no residue. Up to 30% water content can be tolerated in the ethanol and still achieve sufficient strength. The amount of the lotion composition that is applied to the nonwoven may range from 50 to 500 wt %.

Since the towelettes are pre-moistened with a non-aqueous lotion, there is no need for salts that insolubilize the PVOH, such as boric acid and the like, in the binder composition. Thus such insolubilizing salts are excluded from the binder compositions.

The finished towelette or wipes of desired dimensions may be individually packaged, preferably in folded condition, in moisture proof envelopes or in containers holding any desired number of such folded sheets. For individual packaging, it will be convenient to wet the folded sheet with the non-aqueous lotion composition prior to inserting the sheet into the envelope or the composition may be injected into the open envelope which is subsequently sealed. If a number of the wet sheets are to be packaged in a single container which can be closed and reopened for removal of individual towelettes or wipes as needed, the folded sheets may either be pre-moistened with the non-aqueous lotion composition or such composition may be poured over the stacked sheets in the container under conditions assuring appropriate wetting of each of the individual sheets.

Various forms of impermeable envelopes for containing wet-packaged materials such as towelettes, wiping and polishing cloths and the like are well known in the art. Any of these may be employed in packaging the wetted towelettes of the present invention. The envelopes for individual packaging may be formed of any material impervious to the liquid contents. Thus, the envelopes may be made of plastic materials or cellulosic materials lined or coated with plastic or other lotion proof compositions. Preferably, the envelopes should be of a type that can be conveniently opened by tearing to remove the packaged wet towelette.

EXAMPLE 1

The strength of airlaid cellulose bonded at 18% add-on with different binder compositions was measured in ethanol and the disintegration time in water measured quantitatively using the Snag-Breakup test, provided by the National Sanitation Foundation. This test involves folding strips of the nonwoven product around a metal rod and placing the rod in swirling tapwater in a beaker. The time for the cellulosic nonwoven to disintegrate is recorded.

The binder compositions were based on adding various levels of Airvol ® 540 PVOH (87–89 mole % hydrolyzed; DPn=1900) to a vinyl acetate homopolymer emulsion and a vinyl acetate/ethylene copolymer emulsion. Airvol PVOH is marketed by Air Products and Chemicals, Inc. A typical useful wet strength value for pre-moistened wipe of this composition is 300 gli which was achieved at 20 parts PVOH addition for both emulsions. However, higher levels of Airvol 540 PVOH were needed to achieve rapid water disintegration following the ethanol soak. Disintegration times of 1 min or less are considered very rapid and, as can be seen from Table 1, are achieved with approximately 45 parts PVOH to the vinyl acetate homopolymer emulsion. Less than 1 min disintegration time was not achieved with the VAE copolymer emulsion/PVOH blend even at 100 parts PVOH addition levels.

TABLE 1

| Run | Emulsion | A-540$^a$ | Tensile in EtOH | Disintegration |
|---|---|---|---|---|
| 1 | Vinac XX-210$^b$ | 0 | 62 gli | 60+ min |
| 2 | Vinac XX-210$^b$ | 5 | 113 gli | 60+ min |
| 3 | Vinac XX-210$^b$ | 10 | 202 gli | 60+ min |
| 4 | Vinac XX-210$^b$ | 20 | 326 gli | 46 min |
| 5 | Vinac XX-210$^b$ | 40 | 682 gli | 5 min |
| 6 | Vinac XX-210$^b$ | 100 | 1077 gli | <1 min |
| 7 | Airflex 401$^c$ | 0 | 82 gli | 60+ min |
| 8 | Airflex 401$^c$ | 5 | 96 gli | 60+ min |
| 9 | Airflex 401$^c$ | 10 | 118 gli | 60+ min |
| 10 | Airflex 401$^c$ | 20 | 295 gli | 60+ min |
| 11 | Airflex 401$^c$ | 40 | 31 gli | 60+ min |

TABLE 1-continued

| Run | Emulsion | A-540[a] | Tensile in EtOH | Disintegration |
|---|---|---|---|---|
| 12 | Airflex 401[c] | 100 | 1106 gli | 9 min |

[a] Parts PVOH per 100 parts emulsion (solids/solids)
[b] Vinyl acetate homopolymer emulsion
[c] Vinyl acetate/ethylene copolymer emulsion

EXAMPLE 2

In this example Airvol 540 PVOH was blended 50:50 on a dry basis with various polymer emulsion binders in which the polymer had a low Tg to ascertain its impact on the dry hand (feel) of the total binder composition. Tensile strength in ethanol, dry hand (subjectively rated) and disintegration time are shown in Table 2.

TABLE 2

| Run | Emulsion | Tensile in EtOH | Dry Hand | Disintegration |
|---|---|---|---|---|
| 13 | Vinac XX-210 | 1077 gli | 1 (v.stiff) | <1 min |
| 14 | Airflex 401 | 1106 | 2 | 9 |
| 15 | Flexbond 149[a] | 998 | 3 | <1 |
| 16 | Flexbond 153[b] | 1100 | 3 | 60+ |
| 17 | Flexbond 1625[c] | 1066 | 4 (firm) | 9 |

[a] Dioctyl maleate/vinyl acetate copolymer (Tg = −30° C.)
[b] Acrylic/vinyl acetate copolymer (Tg = −40° C.)
[c] Acrylic copolymer (Tg = −40° C.)

The various emulsions were each blended with an equivalent dry weight of Airvol 540 PVOH and used to bond airlaid cellulose at 18% add-on. At this PVOH level, all the emulsion polymer binders in Table 2 showed essentially equivalent strength in ethanol independent of emulsion composition. However, the low Tg binders did soften the hand feel of the bonded nonwoven web. Fast disintegration could be achieved at this level of PVOH for Flexbond 149 emulsion (Run 15), but not for the Flexbond 153 or 1625 emulsions (Runs 16 and 17). Higher levels of PVOH would probably be required to make these emulsions more redispersible.

EXAMPLE 3

The performance of air laid cellulose towelettes bonded with Airvol 540 PVOH at 18% add-on containing lotion compositions is shown in Table 3 compared to two controls. The first control was air laid web bonded with Airflex 109 VAE/NMA emulsion copolymer at 18% add-on and its strength was measured in water. The second control was Airvol 540 PVOH bonded web in 4.5% boric acid solution. The first control represents typical aqueous pre-moistened wipe behavior (commercial baby-wipe performance) and the second control represents a towelette prepared by the insolubilizing salt lotion method. Wet strengths higher than the Airflex 109 emulsion control were achieved in all non-aqueous conditions. The disintegration times are quite fast for both the alcohol and mineral oil runs. The wet hand feel is relatively stiff for the isopropanol and oil runs. This may be acceptable for some abrasive cleansing applications, however, wet hand feel can be softened by incorporation into the lotion of a plasticizer for PVOH, such as glycerine or water as shown in Table 3 while still achieving sufficient strength and disintegration.

TABLE 3

| Run | Lotion | Binder | Wet Tensile | Wet Hand | Disintegration |
|---|---|---|---|---|---|
| 18 | Water | Airflex 109 | 0.6 pli | 6 (soft) | Intact |
| 19 | 4.5% Boric Acid | Airvol 540 | 1.9 | 6 | 1.0 min |
| 20 | Isopropanol | Airvol 540 | 4.1 | 1 | <1 |
| 21 | Ethanol | Airvol 540 | 3.7 | 3 | <1 |
| 22 | Ethanol/Glycerine | Airvol 540 | 2.7 | 4 | <1 |
| 23 | Mineral Oil | Airvol 540 | 6.5 | 1 (stiff) | 2 |

Mineral oil and glycerine are examples of lotion compositions which are not volatile. These lotion bases can function as an active ingredient and it is preferred that they remain as residue on the skin. The residue, however, would not be an unsightly white powder. For example, a hemorrhoid wipe could be manufactured with a mineral oil base used for its skin softening/protection qualities. This wipe, if prepared with the proper choice of PVOH based binder, could then be disposed in the toilet.

EXAMPLE 4

Due to the applicability of pre-moistened/disintegratable towelettes for the cosmetic and medical applications, the same towelette composition as in Example 3, namely an airlaid cellulose towelette bonded with Airvol 540 PVOH at 18% add-on, was evaluated in several commercially available nonaqueous lotion compositions. The webs were saturated in the lotions and their strength, lotionized hand and disintegration times in water are presented in Table 4.

TABLE 4

| Run | Lotion | Lotion Base | Wet Tensile | Hand | Disintegration |
|---|---|---|---|---|---|
| 24 | Bain de Soleil | Oil | 4.85 pli | 2 | 2 min. |
| 25 | Lubriderm | Oil | 5.9 | 1 (stiff) | <1 |
| 26 | Anusol | Oil | 4.5 | 3 | 9+ |
| 27 | Desitin | Oil/Water | 0.3 | 4 (soft) | 30+ |
| 28 | Lectric Shave | Alcohol | 3.0 | 3 | <1 |
| 29 | Clinique | Alcohol/Water | 2.3 | 2 | 11 |
| 30 | Jean Nate | Alcohol/Water | 0.8 | 4 | 3 |
| 31 | Noxema | Alcohol/Water | 0.2 | 4 | 5 |

Unlike the boric acid solution, these lotions do not leave a salt residue on the skin after application. Wet strengths higher than those achieved with the Airflex 109 copolymer bonded control were achieved in almost all cases except for the nonwovens comprising the Desitin and Noxema lotions which presumably contain high water levels. The water was, however, effective at softening the wet hand feel of the towelette. While all the webs eventually disintegrated, the disintegration times for the nonwovens comprising Lubriderm and Lectric Shave lotions were quite fast.

The range of commercial lotions applicable to this invention and disintegration performance indicate that a variety of products other than "flushable" could be beneficial. These may include wipe products used in outdoor activities such as camping, biking, hiking, boating, and swimming. These products, if discarded as litter, would be disintegrated by rain or stream/lake/ocean water and not remain visible in the environment.

The compositions of the lotions as stated on the commercial packages are shown in Table 5.

TABLE 5

| PRODUCT | COMPANY | INGREDIENTS |
| --- | --- | --- |
| Bain de Soleil Deep Tanning Oil SPF 2 | Richardson-Vicks Inc. | mineral oil, sesame oil, isopropyl myristate, sorbitan oleate, fragrance, propyl paraben, propylene glycol, BHA, propyl gallate, padimate O, citric acid, D&C red #17 |
| Noxema Antiseptic Skin Cleanser | Noxell Corp. | SD alcohol 40 (40.6%), water, PPG-11 stearyl ether, menthol, camphor, clove oil, eucalyptus oil, fragrance, FD&C blue #1 |
| Jean Nate After Bath Splash | Revlon, Inc. | SD alcohol 40-B, water, fragrance, benzophenone-2, FD&C yellow #6, FD&C blue #1 |
| Williams Lectric Shave Unscented | Beecham Inc. | SD alcohol 40, isopropyl alcohol, isopropylmyristate, phenyl trimethicone |
| Lubriderm Skin Conditioning Oil | Warner Lambert | mineral oil. PPG-15, stearyl ether oleth-2, nonoxy-nol-5, fragrance, D&C green #6 |
| Clinique Clarifying Lotion 2 | Clinique Labs Inc. | SD alcohol 40, water, witch hazel, glycerin, acetone, sodium borate, menthol, caramel, D&C red #33 |
| Anusol Hemorrhoidal Ointment | Parke-Davis Div. Warner Lambert Co. | calcium phosphate DB, cocoa butter, glyceryl monooleate, glyceryl monostearate, kaolin, mineral oil, polyethylene wax, pramoxine hydrochloride, zinc oxide, benzyl benzoate, peruvian balsam |
| Desitin Diaper Rash Ointment | Leeming Div. of Pfizer Inc. | zinc oxide (40%), BHA, cod liver oil, fragrances, lanolin, methylparaben, petrolatum, talc, water |

As can be seen from the date in Tables 1-4, towelettes have been made which show very high strength in the nonaqueous lotion compositions. These towelettes also rapidly disintegrate in plain water. Key examples of such pre-moistened towelettes include airlaid pulp nonwoven web bonded with the following: 1:1 blends of Vinac XX-210 emulsion and Airvol 540 PVOH packaged in ethanol; 1:1 blends of Flexbond 149 emulsion and Airvol 540 PVOH in ethanol which shows improved hand feel; and Airvol 540 PVOH in isopropanol, ethanol and mineral oil lotions.

Table 4 which shows Airvol 540 PVOH bonded wipes in Desitin and Noxema lotions have low strength values due to high water contents. The Airvol 540 PVOH wipes in Desitin and Clinique showed long disintegration time due to the very thick, water-resistant lotion formulation in the former case and the presence of borax in the lotion in the latter case.

It is believed that the present invention works because of the solubility behavior of PVOH. PVOH is not soluble in many solvents and salt solutions but is soluble in water. This allows the formulation of a variety of lotion compositions in which the nonwoven web can exhibit good strength. However, upon exposure to water the web will rapidly disintegrate.

STATEMENT OF INDUSTRIAL APPLICATION

The invention provides PVOH containing binder formulations for use in conjunction with non-aqueous lotion compositions to produce a pre-moistened wipe which will rapidly disintegrate in water and not leave a salt residue.

I claim:

1. In a packaged towelette composed of a sheet of non-woven fiber impregnated with a binder which is a polyvinyl alcohol or an emulsion polymer binder containing polyvinyl alcohol as a protective colloid, the sheet being maintained in a wet condition within the package, the improvement which comprises the sheet being maintained in a wet condition within the package by contact with a non-aqueous lotion composition comprising a liquid organic compound that is a nonsolvent for polyvinyl alcohol selected from the group consisting of hydrocarbons, halogenated hydrocarbons, $C_1$-$C_3$ alcohols, tetrahydrofuran, dioxane, ethylene glycol formal, ketones, carboxylic acids, esters, and ethyl lactate.

2. The packaged towelette of claim 1 in which the liquid organic compound is selected from the group consisting of methanol, ethanol, i-propanol and n-propanol.

3. The packaged towelette of claim 1 in which the liquid organic compound is ethanol.

4. The packaged towelette of claim 1 in which the towelette has a wet tensile strength value greater than 300 grams per linear inch.

5. The packaged towelette of claim 1 in which the towelette has a disintegration time in water of less than 1 minute.

6. A premoistened, packaged towelette comprising a sheet of nonwoven fiber impregnated with a binder which is a 75-90 mole % hydrolyzed polyvinyl alcohol having a degree of polymerization of greater than 600 or a vinyl acetate or vinyl acetate/ethylene emulsion polymer binder containing polyvinyl alcohol as a protective colloid, the sheet being maintained in a wet condition within the package by contact with a non-aqueous lotion composition comprising a liquid organic compound that is a nonsolvent for polyvinyl alcohol in the absence of salts that insolubilize the polyvinyl alcohol, the liquid organic compound selected from the group consisting of hydrocarbons, halogenated hydrocarbons, $C_1$-$C_3$ alcohols, tetrahydrofuran, dioxane, ethylene glycol formal, ketones, carboxylic aids, esters, and ethyl lactate, the amount of binder being at least sufficient to bind the nonwoven fibers together.

7. The towelette of claim 6 in which the liquid organic compound is selected from the group consisting of methanol, ethanol, i-propanol and n-propanol.

8. The towelette of claim 6 in which the liquid organic compound is ethanol.

9. The towelette of claim 6 in which the towelette has a wet tensile strength value greater than 300 grams per linear inch.

10. The towelette of claim 9 in which the towelette has a disintegration time in water of less than 1 minute.

* * * * *